United States Patent [19]

Lee

[11] 4,299,825

[45] Nov. 10, 1981

[54] CONCENTRATED XANTHAN GUM SOLUTIONS

[75] Inventor: Ho-Lun Lee, New Providence, N.J.

[73] Assignee: Celanese Corporation, New York, N.Y.

[21] Appl. No.: 165,478

[22] Filed: Jul. 3, 1980

[51] Int. Cl.$^3$ .................. A61K 31/70; E21B 43/22
[52] U.S. Cl. .................................. 424/180; 536/114; 252/8.55 D; 435/104
[58] Field of Search ............ 424/180; 435/104; 536/1, 114; 252/8.55 D

[56] References Cited

U.S. PATENT DOCUMENTS

| | | | |
|---|---|---|---|
| 3,355,447 | 11/1967 | O'Connell | 536/1 |
| 4,119,491 | 10/1978 | Wellington | 536/114 |
| 4,119,546 | 10/1978 | Wernau | 536/114 |
| 4,135,979 | 1/1979 | Corley et al. | 536/114 |

*Primary Examiner*—Johnnie R. Brown
*Assistant Examiner*—Blondel Hazel

[57] ABSTRACT

This invention provides a process for clarifying and concentrating Xanthomonas heteropolysaccharide fermentation broth, which process includes filtration and ultrafiltration steps.

A clarified and concentrated xanthan gum solution of the present invention contains between about 8–15 weight percent xanthan gum, and exhibits a viscosity in the range of 15,000–30,000 centipoises, and a light transmittance of greater than 5 percent as measured by a colorimeter.

16 Claims, No Drawings

CONCENTRATED XANTHAN GUM SOLUTIONS

BACKGROUND OF THE INVENTION

The fermentation of carbohydrates to produce biosynthetic water-soluble gums by the action of Xanthomonas bacteria is well known. The earliest work in this field was conducted by the U.S. Department of Agriculture and is described in U.S. Pat. No. 3,000,790. Particularly well known is the action of *Xanthomonas campestris* NRRL B-1459 on a glucose substrate.

Xanthomonas hydrophilic colloid (i.e., xanthan gum) is produced by transferring *Xanthomonas campestris* bacteria to a suitable medium and conditioning it to growth through two steps before allowing it to grow in a final medium containing 3 percent glucose. After 96 hours at 30° C. with suitable aeration and stirring, Xanthomonas hydrophilic colloid is produced in approximately 1 percent concentration. Modified fermentation processes are described in U.S. Pat. Nos. 3,391,060; 3,391,061; 3,427,226; 3,455,786; 3,565,763; and the like.

Xanthomonas hydrophilic colloid is a microbial heteropolysaccharide which contains mannose, glucose, glucuronic acid, O-acetyl radicals and acetal-linked pyruvic acid in a molar ratio of 2:2:1:1:0.5.

While *Xanthomonas campestris* is the bacteria of choice for the purpose of producing the biosynthetic Xanthomonas hydrophilic colloid, other Xanthomonas species may be employed such as *X. begoniae, X. malvacearum, X. carotae, X. incanae, X. phaseoli, X. vesicatoria, X. papavericola, X. translucens, X. vasculorum,* and *X. hedrae.*

A typical raw fermentation broth is a viscous pseudoplastic solution containing between about 0.5-4 weight percent of microbial heteropolysaccharide, in addition to small amounts of salts, unreacted carbohydrate, Xanthomonas cells and other insoluble debris. The insoluble solids are difficult to remove from the heteropolysaccharide-containing broth, and their presence results in cloudy suspensions rather than clear solutions. For most applications, the presence of insoluble impurities in heteropolysaccharide-containing broths is undesirable. For example, such impurities tend to plug subterranean formations when an aqueous solution of a heteropolysaccharide is employed for oil recovery by water-flooding. Any attempt to clarify a heteropolysaccharide solution at an oil-well site is difficult and prohibitively expensive.

In a typical process for clarification of a Xanthomonas fermentation broth and/or recovery of the Xanthomonas hydrocolloid component, the broth is diluted with water to reduce its viscosity, and optionally the diluted broth is centrifuged or filtered to remove suspended insoluble solids. A salt such as potassium chloride and a nonsolvent such as methanol or isopropanol are added to the broth to flocculate the gum in the potassium form, which gum is then recovered by centrifugation or other solid/liquid separation technique. Further dissolution, reprecipitating and washing steps are usually employed.

U.S. Pat. No. 3,355,447 describes a process for treating a Xanthomonas hydrophilic colloid to improve its stability which involves heating an aqueous solution of the colloid at a temperature of 150°-170° F. for at least 20 minutes, cooling the heated solution to a temperature of 40°-100° F., adjusting the concentration of the medium to provide not more than about 1 percent by weight of colloid, and filtering the medium to recover a clarified hydrophilic colloid solution.

U.S. Pat. No. 3,516,983 describes a process for purifying a Xanthomonas hydrophilic colloid medium containing proteinaceous impurities which involves maintaining the pH of the aqueous medium above about 8, adding an alkali metal hypochlorite to the mixture, adjusting the pH of the medium to slightly acidic, and then adding a lower alcohol to precipitate the Xanthomonas hydrophilic colloid.

U.S. Pat. No. 3,591,578 describes an improved process for recovering a polysaccharide from a fermentation broth by precipitation, which involves heating the broth at a temperature of 80°-130° C. for a period of 10-110 minutes of a pH of 6.3-6.9 prior to precipitation.

U.S. Pat. No. 3,773,752 describes a method for recovering a microbial polysaccharide produced by Xanthomonas bacteria which involves diluting the fermentation broth with an alkaline metal salt solution to coagulate the insoluble solids which are present, and thereafter removing the coagulated solids by filtration.

U.S. Pat. No. 3,919,189 describes a method of decreasing the bacterial contamination of xanthan gum by treatment of the gum with propylene oxide gas.

U.S. Pat. No. 3,966,618 describes a method of clarifying a fermentation broth which contains dissolved xanthan gum and suspended solids which involves treating the broth with a minor amount of a protease enzyme. U.S. Pat. No. 4,010,071 and U.S. Pat. No. 4,119,491 also describe methods of broth clarification by means of protease enzyme treatment. U.S. Pat. No. 4,051,317 describes a method of precipitating xanthan gum from an aqueous solution which involves adding an aluminum salt to the aqueous solution, and thereafter increasing the pH of the solution to 3.5-4.5.

U.S. Pat. No. 4,094,739 describes a method for removing bacterial cells from an aqueous mixture containing a polysaccharide produced by bacterial fermentation, which method involves the steps of killing the said bacterial cells, and then causing the aqueous mixture to undergo a second fermentation with a Trichoderma sp. mold to effect solubilization of the said killed cells.

U.S. Pat. No. 4,135,979 describes a method for clarifying a xanthan gum fermentation broth which involves heating the broth and filtering the broth while maintaining it at a temperature of 112°-160° C., wherein the broth contains at least about 1.5 weight percent of xanthan gum.

In most of the prior art procedures involving clarification and purification treatment of bacterial fermentation broths, the resultant biosynthetic heteropolysaccharide product is recovered either as a soluble component of a very dilute solution, or in the form of a recovered solid precipitate. A dilute solution is a disadvantage because it cannot be shipped economically. A solid precipitate is a disadvantage because it must be redissolved for purposes of most applications such as secondary and tertiary petroleum recovery processes.

Accordingly, it is an object of this invention to provide an improved process for producing a clarified biosynthetic heteropolysaccharide fermentation broth.

It is another object of this invention to provide a process for producing a concentrated solution of Xanthomonas hydrophilic colloid.

It is a further object of this invention to provide a clarified Xanthomonas fermentation broth containing at least about 8 weight percent of dissolved xanthan gum, and having a viscosity between about 10,000–20,000 centipoises.

Other objects and advantages of the present invention shall become apparent from the accompanying description and example.

DESCRIPTION OF THE INVENTION

As described more fully hereinbelow, one or more objects of the present invention are accomplished by the provision of a process embodiment for clarifying and concentrating raw Xanthomonas heteropolysaccharide fermentation broth which comprises (1) filtering the broth to remove substantially all of the insoluble fermentation solids and provide a clarified solution containing between about 0.1–3 weight percent of xanthan gum; and (2) subjecting the clarified xanthan gum solution to ultrafiltration to yield a clarified and concentrated xanthan gum solution which contains between about 8–15 weight percent of xanthan gum, and which exhibits a solution viscosity between about 10,000–20,000 centipoises.

In another embodiment, this invention provides a process for clarifying and concentrating raw Xanthomonas heteropolysaccharide fermentation broth which comprises (1) heating the fermentation broth at a temperature between about 60°–150° C. for a period of time between about 0.3–3 hours; (2) filtering the broth to remove substantially all of the insoluble fermentation solids and provide a clarified solution containing between about 0.1–3 weight percent of xanthan gum; and (3) subjecting the clarified xanthan gum solution to ultrafiltration to yield a clarified and concentrated xanthan gum solution which contains between about 8–15 percent of xanthan gum, and which exhibits a solution viscosity between about 10,000–20,000 centipoises.

In a further embodiment, this invention provides a process for clarifying and concentrating Xanthomonas hydrophilic colloid fermentation broth which comprises (1) adjusting the volume of the fermentation broth to provide a broth which contains between about 0.1–1 weight percent of xanthan gum; (2) heating the broth at a temperature between about 70°–110° C. for a period of time between about 0.5–2 hours; (3) filtering the broth to remove substantially all of the insoluble fermentation solids and provide a clarified solution of xanthan gum; and (4) subjecting the clarified xanthan gum solution to ultrafiltration to yield a clarified and concentrated xanthan gum solution which contains between about 8–15 weight percent of xanthan gum, and which exhibits a solution viscosity between about 10,000–20,000 centipoises.

Viscosities referred to in the present specification and claims are in centipoises measured at 25° C. with a Brookfield Viscometer Model LVF, spindle No. 4, at 20 rpm.

XANTHOMONAS FERMENTATION BROTH

As described in U.S. Pat. No. 3,516,983 and 4,135,979, Xanthomonas hydrophilic colloid can be biosynthesized by whole culture *Xanthomonas campestris* fermentation of a medium containing 2–5 percent of commercial glucose, an organic nitrogen source, dipotassium hydrogen phosphate, and appropriate trace elements.

The incubation time of the final medium is approximately 96 hours at 30° C. under aerobic conditions. In preparing the colloid, it is convenient to use corn steep liquor or distillers' dry solubles as an organic nitrogen source. It is convenient to grow the culture in two intermediate stages prior to the final inoculation in order to encourage vigorous growth of the bacteria. These stages may be carried out in media having a pH of about 7.

In the first stage a transfer from an agar slant to a dilute glucose broth may be made and the bacteria cultured for 24 hours under vigorous agitation and aeration at a temperature of about 30° C. The culture so produced may then be used to inoculate a higher glucose (3%) content broth of larger volume in a second intermediate stage. In this stage the reaction may be permitted to continue for 24 hours under the same conditions as the first stage. The culture so acclimated for use with glucose by the first and second stages is then added to the final glucose medium. In the said method of preparing *Xanthomonas campestris* hydrophilic colloid, a loopful of organism from the agar slant is adequate for the first stage comprising 290 milliliters of the glucose medium. In the second stage, the material resulting from the first stage may be used together with 9 times its volume of 3 percent glucose medium.

In the final stage the material produced in the second stage may be admixed with 19 times its volume of the final medium. A good final medium may contain 3 percent glucose, 0.5 percent distillers' solubles, 0.5 percent dipotassium phosphate, 0.1 percent magnesium sulphate having 7 molecules of water of crystallization, and water. The reaction in the final stage may be satisfactorily carried out for 96 hours at 30° C. with vigorous agitation and aeration.

The resultant raw Xanthomonas hydrophilic colloid fermentation liquor is referred to as a fermentation beer or a fermentation broth. A typical raw fermentation broth contains between about 0.5–4 weight percent of dissolved Xanthomonas hydrophilic colloid, and has a viscosity in the range between about 500–50,000 cps at room temperature.

XANTHOMONAS FERMENTATION BROTH FILTRATION

A raw Xanthomonas fermentation broth contains an insoluble solids suspension phase which includes components such as bacterial cellular debris, salts, unconverted carbohydrates, and the like. These extraneous insoluble fermentation solids are undesirable because they contribute objectionable odor, color and unstability of hydrophilic colloid solutions. Further, in applications such as oil well flooding operations, hydrophilic colloid solutions must be substantially free of undissolved solids. Foodstuff, cosmetic and pharmaceutical applications also may sometimes require a highly clarified hydrophilic colloid product.

For purposes of the present invention, a raw Xanthomonas fermentation broth is subjected to a filtration procedure to remove substantially all of the insoluble fermentation solids and provide a clarified solution containing between about 0.1–3 weight percent of xanthan gum. The pH of the clarified solution normally will be in the range between about 6–9. The pH of the clarified solution can be adjusted as desired by the appropriate addition of acid or base.

The filtration operation preferably is accomplished with commercially available filter aids such as diatomaceous earth. A convenient clarification procedure is by filtration of fermentation broth through a pressure leaf filter coated with a slurry of a diatomaceous earth filter aid such as Johns-Manville Super-Cel.

The insoluble fermentation solids suspension which is removed by filtration constitutes about 20 weight percent of the solids content of the original raw fermentation broth before filtration.

As disclosed previously hereinabove, in an important embodiment of the present invention the raw fermentation broth is heated at a temperature between about 60°–150° C. for a period of time between about 0.3–3 hours prior to the filtration procedure. Further, the efficiency of the filtration is improved if the temperature of the fermentation broth is maintained in the range between about 40°–100° C. during the filtration operation.

It has also been found that a superior clarified xanthan gum solution is obtained if the raw fermentation broth is subjected to both high shear agitation and heating prior to the filtration step. For example, one apparent effect of high shear mixing and heating prior to filtration is a deflocculation of the colloidal solution. The deflocculation alleviates the problem of filter plugging and results in faster filtration of the hydrophilic colloid medium.

It has also been found that additional advantage is achieved if the volume of the raw Xanthomonas fermentation broth is adjusted to provide a broth which contains between about 0.1–1 weight percent of xanthan gum, wherein the volume dilution is effected prior to any of the heating and high shear mixing and filtration steps of the invention process.

ULTRAFILTRATION OF CLARIFIED XANTHAN GUM SOLUTION

Ultrafiltration is a process of separation in which a solution containing a solute of high molecular weight is separated from a solvent of low molecular weight, wherein the solvent is depleted of the solute when the solvent is forced through a semipermeable membrane under pressure.

The semipermeable membrane is characterized by a microporous structure in which the apparent pore diameter averages in the range between about 1–500 millimicrons, and the average thickness of the membrane is in the range between about 0.1–5 microns. For the purposes of the present invention process, nominally the microporous structure of the membrane has an average pore size sufficient to reject solute molecules having a molecular weight above about 10,000.

Suitable membranes include inorganic and organic polymeric materials, ceramics, glass frits, porous metals, graphite, and the like. Preferred membranes are those which exhibit (1) high hydraulic permeability to solvent at a pressure between about 30–250 psi; (2) sharp retention cut-off of solute molecules having a molecular weight above about 10,000; (3) good mechanical durability under operating condition; and (4) high fouling resistance.

Among the most preferred ultrafiltration membranes are those prepared from film forming polymeric substrates such as cellulose esters, cellulose ethers, phenolaldehyde, urea-aldehyde, acrylics, polyamides, polyolefins, silicone rubbers, polystyrenes, sulfonated polystyrenes, and the like.

Ultrafiltration equipment and techniques are described in prior art references which include U.S. Pat. Nos. 3,488,768; 3,508,994; 3,541,006; 3,556,302; 3,556,992; 3,565,256; 3,566,305; 3,567,377; 3,567,810; 3,808,305; 3,856,569; 4,000,065; 4,082,659; and the like.

Also of interest are publications such as "Membrane Ultrafiltration," Chemical Technology, 56 (January 1971), and Chemical Engineering Progress, 64, No. 12, 31 (1968).

Particularly noteworthy prior art with respect to the present invention are U.S. Pat. Nos. 2,128,551; 3,541,006; 3,549,016; 3,567,810; and 3,856,569 which describe the ultrafiltration of aqueous solutions of polysaccharides such as dextran, carrageenans, aginates, and the like.

The ultrafiltration step of the present invention process can be accomplished by employing a commercially available unit, such as one containing either a flat sheet or hollow fiber type of membrane, as manufactured by companies such as Abcor Inc. (Wilmington, Mass.) and Amicon Corp. (Lexington, Mass.).

In accordance with the present invention process, Xanthomonas fermentation broth which is free of insoluble solids (i.e., a clarified xanthan gum solution) is subjected to ultrafiltration to yield a clarified and concentrated xanthan gum solution which contains between about 8–15 weight percent of xanthan gum.

In addition to reducing the volume of water, the ultrafiltration treatment removes other solute components from the solution which have a molecular weight sufficiently low to allow passage through the semipermeable membrane, e.g., molecules of molecular weight less than about 5000. The solute components include organic compounds such as carboxylic acids, esters and sugars, and inorganic components such as dibasic sodium phosphate.

The present invention combination of filtration and ultrafiltration steps provides a novel type of clarified and concentrated xanthan gum solution which has a unique combination of properties.

First, the solution contains an exceptionally high content of xanthan gum, i.e., a content of between about 8–15 weight percent of xanthan gum. As it is apparent, this novel type of concentrated solution of xanthan gum has economic advantages when being stored or transported.

Second, the concentrated xanthan gum solution exhibits exceptional clarity and low particle count under an optical microscope (900X). It has a light transmittance of greater than 5 percent as measured by colorimetry, and a particle count of not greater than $10^9$ particles per cubic centimeter. This qualifies the xanthan gum product for incorporation in foodstuffs, drugs and cosmetics, and for use as a thickening agent in oil well recovery operations.

Third, the clarified and concentrated xanthan gum solution exhibits a relatively low viscosity range, i.e., a viscosity in the range between about 10,000–20,000 cps. Thus, the viscosity of a present invention concentrated solution containing about 9.5 percent xanthan gum is only 40 percent of that for concentrated raw fermentation broth which contains about 6.8 percent xanthan gum plus other solids. This corresponds to viscosities of about 15,000 cps and 36,000 cps, respectively. At a 9.5 weight percent level, a typical invention xanthan gum solution is pourable at room temperature. At a 6.8 weight percent solids level, a raw Xanthomonas fermentation broth mixture is a firm gel at room temperature.

It is a particularly important aspect of an invention xanthan gum solution that it has a relatively low viscosity in concentrated form (e.g., 15 weight percent xanthan gum), and a relatively high viscosity in dilute form (e.g., 0.2 weight percent xanthan gum).

An invention xanthan gum solution is characterized by the following viscosity/concentration profile for a concentration range of 0.05–15 weight percent xanthan gum:

| Weight % | Viscosity, centipoises |
|---|---|
| 15 | 10,000–20,000 |
| 12 | 9000–17,000 |
| 10 | 7000–15,000 |
| 8 | 6000–10,000 |
| 6 | 5000–8000 |
| 4 | 3500–6000 |
| 2 | 2000–3000 |
| 1 | 1300–1800 |
| 0.8 | 1000–1400 |
| 0.6 | 800–1100 |
| 0.4 | 600–740 |
| 0.2 | 370–430 |
| 0.1 | 280–180 |
| 0.05 | 50–200 |

It is believed that the above represented viscosity/concentration profile is a novel property for a xanthan gum solution, one that has not been reported previously in the prior art. This novel property provides important advantages.

Thus, the relatively low viscosity of an invention 15 percent xanthan gum solution (i.e., 10,000–20,000 cps) facilitates the transfer of the material, such as in pumping operations. The said concentrated xanthan gum solution is readily amenable to dilution with water.

The relatively high viscosity of an invention dilute xanthan gum solution permits its effective use as a thickening agent, even at a low concentration as compared to xanthan gum contained in a typical fermentation broth. For example, an invention 0.2 percent xanthan gum solution has a nominal viscosity of about 400 cps, and a corresponding 0.2 percent xanthan gum fermentation broth has a nominal viscosity of about 280 cps.

HIGH PURITY XANTHAN GUM SOLIDS

In another of its embodiments, this invention contemplates the precipitation and recovery of high purity xanthan gum solids from a clarified and concentrated xanthan gum solution.

The precipitation can be effected by diluting the xanthan gum solution with a water-soluble medium such as methanol, ethanol, isopropanol, tertiary-butanol, acetone, tetrahydrofuran, and the like. When employing methanol or ethanol as the precipitating diluent, it is advantageous to include an electrolyte such as potassium chloride or sodium chloride.

The precipitating diluent is employed in a quantity between about 0.5–1.5 volumes per volume of xanthan gum solution. After separation of the precipitated xanthan gum solids from the aqueous medium by filtration or centrifugation, normally the xanthan gum solids are dried and milled.

The following Example is further illustrative of the present invention. The specific ingredients are presented as being typical, and various modifications can be derived in view of the foregoing disclosure within the scope of the invention.

EXAMPLE

A xanthan gum fermentation broth is prepared under biosynthesis conditions by a xanthomonas genus of bacteria operating on a substrate of glucose or equivalent sugar, in a manner as illustrated in prior art such as U.S. Pat. Nos. 3,000,790; 3,020,207 and 3,557,016.

The volume of the fermentation broth is diluted with water to provide a broth containing about 0.4 weight percent xanthan gum (a nominal viscosity of 500 cps at 25° C., Brookfield Viscometer Model LVF, spindle No. 4 at 20 rpm).

Approximately 2 grams of Superaid (diatomaceous earth, Johns-Manville) per liter is added to the broth, and the slurry mixture is stirred with a high shear mixer (Dispax) for two hours. The slurry mixture is heated to 90°–100° C. and the high shear stirring is continued for another hour. The slurry mixture is filtered through a 0.045 gm/cm$^2$ precoat of Superfloss (diatomaceous earth, Johns-Manville). The resultant clarified solution has a light transmittance of greater than 90 percent as measured on a Brinkmann Colorimeter (Model No. PC/600).

The clarified solution (25 liters) is ultrafiltered with an Abcor flat-sheet membrane in a flow-through test cell unit. The total membrane area is 5 square inches, and the operating time is 84.5 hours. About 22.5 liters of water is removed with an average flux of 46 GFD (gallons/ft$^2$/day). The resultant concentration of the xanthan gum is 4 weight percent.

Employing the same procedure, a 120 liter quantity of clarified broth solution is prepared which contains about 0.5 weight percent of xanthan gum.

Ultrafiltration of the solution is performed continuously over a period of 53 hours, with the removal of about 114 liters of aqueous permeate. The average flow rate is 34.6 cm$^3$/min, which corresponds to an average flux of about 42 GFD. The resultant clarified xanthan gum concentrate contains about 9.5 weight percent of xanthan gum, has a nominal viscosity of about 15,000 centipoises, and has a light transmittance of greater than 90 percent as determined on a Brinkmann Colorimeter.

For comparison purposes, an untreated raw fermentation broth containing about 2.6 weight percent of xanthan gum is subjected to the same ultrafiltration procedure as described above. It is found that the maximum concentration that can be achieved is about 6.8 weight percent of xanthan gum content, because of high viscosity limitations. At the 6.8 weight percent level, the concentrate mixture has the properties of a firm gel (36,000 centipoises).

What is claimed is:

1. A process for clarifying and concentrating raw Xanthomonas heteropolysaccharide fermentation broth which comprises (1) filtering the broth to remove substantially all of the insoluble fermentation solids and provide a clarified solution containing between about 0.1–3 weight percent of xanthan gum; and (2) subjecting the clarified xanthan gum solution to ultrafiltration to yield a clarified and concentrated xanthan gum solution which contains between about 8–15 weight percent of xanthan gum, and which exhibits a solution viscosity between about 10,000–20,000 centipoises.

2. A process in accordance with claim 1 wherein the step (1) filtration medium is diatomaceous earth.

3. A process in accordance with claim 1 wherein the insoluble fermentation solids constitute up to about 20 weight percent of the total solids content of the fermentation broth.

4. A process in accordance with claim 1 wherein the clarified and concentrated xanthan gum solution in step (2) contains between about 10–12 weight percent of xanthan gum, and the solution viscosity is between about 15,000–17,000 centipoises.

5. A process for clarifying and concentrating raw Xanthomonas heteropolysaccharide fermentation broth which comprises (1) heating the fermentation broth at a temperature between about 60°–150° C. for a period of time between about 0.3–3 hours; (2) filtering the broth to remove substantially all of the insoluble fermentation solids and provide a clarified solution containing between about 0.1–3 weight percent of xanthan gum; and (3) subjecting the clarified xanthan gum solution to ultrafiltration to yield a clarified and concentrated xanthan gum solution which contains between about 8–15 weight percent of xanthan gum, and which exhibits a solution viscosity between about 10,000–20,000 centipoises.

6. A process in accordance with claim 5 wherein the step (2) filtration medium is diatomaceous earth.

7. A process in accordance with claim 5 wherein the clarified and concentrated xanthan gum solution in step(3) contains between about 10–12 weight percent of xanthan gum, and the solution viscosity is between about 15,000–17,000 centipoises.

8. A process for clarifying and concentrating Xanthomonas hydrophilic colloid fermentation broth which comprises (1) adjusting the volume of the fermentation broth to provide a broth which contains between about 0.1–1 weight percent of xanthan gum; (2) heating the broth at a temperature between about 70°–110° C. for a period of time between about 0.5–2 hours; (3) filtering the broth to remove substantially all of the insoluble fermentation solids and provide a clarified solution of xanthan gum; and (4) subjecting the clarified xanthan gum solution to ultrafiltration to yield a clarified and concentrated xanthan gum solution which contains between about 8–15 weight percent of xanthan gum, and which exhibits a solution viscosity between about 10,000–20,000 centipoises.

9. A process in accordance with claim 8 wherein the broth in step(2) is subjected to high shear stirring during the heating period.

10. A process in accordance with claim 8 wherein the step(3) filtration medium is diatomaceous earth.

11. A process in accordance with claim 8 wherein the temperature of the fermentation broth is about 40°–100° C. during the step(3) filtration procedure.

12. A xanthan gum solution containing between about 8–15 weight percent of xanthan gum, which solution exhibits a viscosity between about 10,000–20,000 centipoises, and is characterized by the following viscosity/concentration profile:

| Weight % | Viscosity, centipoises |
|---|---|
| 15 | 10,000–20,000 |
| 12 | 9000–17,000 |
| 10 | 7000–15,000 |
| 8 | 6000–10,000 |
| 6 | 5000–8000 |
| 4 | 3500–6000 |
| 2 | 2000–3000 |
| 1 | 1300–1800 |
| 0.8 | 1000–1400 |
| 0.6 | 800–1100 |
| 0.4 | 600–740 |
| 0.2 | 370–430 |
| 0.1 | 280–180 |
| 0.05 | 50–200 |

13. A xanthan gum solution in accordance with claim 12 which exhibits a light transmittance of greater than about 5 percent as measured by colorimetry.

14. A xanthan gum solution in accordance with claim 12 which exhibits a particle count of not greater than about $10^9$ particles per cubic centimeter under an optical microscope.

15. A process for recovering high purity xanthan gum solids from raw Xanthomonas heteropolysaccharide fermentation broth which comprises (1) filtering the broth to remove substantially all of the insoluble fermentation solids and provide a clarified solution containing between about 0.1–3 weight percent of xanthan gum; (2) subjecting the clarified xanthan gum solution to ultrafiltration to yield a clarified and concentrated xanthan gum solution which contains between about 8–15 weight percent of xanthan gum, and which exhibits a solution viscosity between about 10,000–20,000 centipoises; (3) diluting the clarified and concentrated xanthan gum solution with a water-soluble solvent medium to precipitate xanthan gum solids from the said solution; and (4) separating and recovering the precipitated xanthan gum solids.

16. A process in accordance with claim 15 wherein the water-soluble solvent medium in step(3) is a water-soluble alcohol.

* * * * *